United States Patent [19]

Mizutani et al.

[11] 4,162,269

[45] Jul. 24, 1979

[54] PURIFICATION PROCESS FOR 3-PHENOXYBENZALDEHYDE

[75] Inventors: Masato Mizutani, Takarazuka; Akio Higo, Osaka; Nobuo Ohno, Toyonaka; Hajime Hirai, Nishinomiya, all of Japan

[73] Assignee: Sumitomo Chemical Company, Limited, Osaka, Japan

[21] Appl. No.: 825,154

[22] Filed: Aug. 16, 1977

[30] Foreign Application Priority Data

Aug. 20, 1976 [JP] Japan ................................. 51/100040

[51] Int. Cl.$^2$ ............................................. C07C 45/24
[52] U.S. Cl. ............................................. 260/600 R
[58] Field of Search ........... 260/600 R, 601, 567.6 M, 260/599, 600 RS

[56] References Cited

U.S. PATENT DOCUMENTS

| 4,041,081 | 8/1977 | Bexten et al. ..................... 260/601 R |
| 4,065,505 | 12/1977 | Kim et al. ........................ 260/600 R |

OTHER PUBLICATIONS

Lock et al., Monatshe, Chem., vol. 67 (1935) pp. 24–35.
Starks, JACS, vol. 93 (1971) 195–199.

*Primary Examiner*—Bernard Helfin
*Attorney, Agent, or Firm*—Stevens, Davis, Miller & Mosher

[57] ABSTRACT

A purification process for 3-phenoxybenzaldehyde, which comprises reacting crude 3-phenoxybenzaldehyde with an alkali metal or ammonium bisulfite, or metabisulfite in the presence of an organic quaternary ammonium salt, an inorganic acid salt of organic tertiary amines, or a macrocyclic polyether used as a catalyst, isolating the resulting 3-phenoxybenzaldehyde alkali metal or ammonium bisulfite adduct, and decomposing it by using an acid or a base, or by heating.

3 Claims, No Drawings

PURIFICATION PROCESS FOR 3-PHENOXYBENZALDEHYDE

This invention relates to a purification process for 3-phenoxybenzaldehyde, characterized by reacting crude 3-phenoxybenzaldehyde with an alkali metal or ammonium bisulfite, or metabisulfite, in the presence of an organic quaternary ammonium salt, an inorganic acid salt of organic tertiary amines, or a macrocyclic polyether used as a catalyst, isolating the resulting 3-phenoxybenzaldehyde alkali metal or ammonium bisulfite adduct, and decomposing it by using an acid or a base, or by heating.

3-Phenoxybenzaldehyde purified according to the process of this invention is an important intermediate in the synthesis of α-cyano-3-phenoxybenzyl α'-substitutedphenylacetates represented by the formula (A) [Japanese Patent Application "Kokai" (Laid-Open) No. 26,425/74 and No. 126,826/74], α-cyano-3-phenoxybenzyl cyclopropanecarboxylates represented by the formula (B) [Nature, 248, 710 (1974)], 3-phenoxybenzyl chrysanthemate represented by the formula (C) (Japanese Patent Publication No. 21,473/71) and the like which have excellent insecticidal activity.

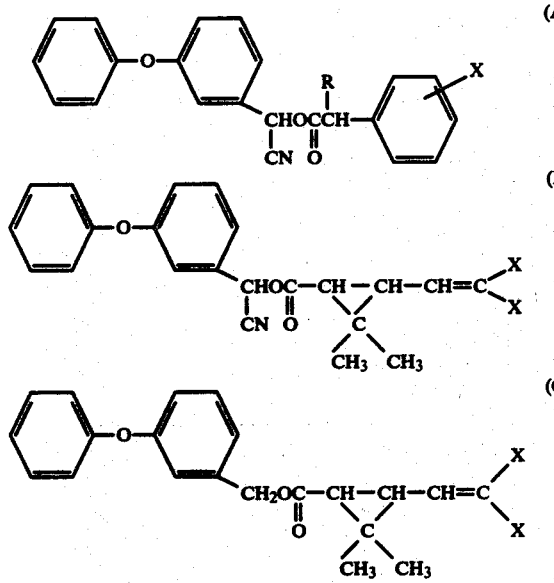

Synthesis of 3-phenoxybenzaldehyde can be carried out in various ways according to the general methods for producing aldehydes, but the quality of the product is not sufficient for use as an intermediate in synthesizing the above various insecticidal compounds. For instance, the reaction product obtained by the Sommelet reaction from 3-phenoxytoluene having a halogen atom substituted in the side chain and urotropin contains from 75% to 80% of 3-phenoxybenzaldehyde and 20% or more of non-aldehyde compounds (Reference Example 1). Accordingly, in order that the reaction product be usable as an intermediate in synthesizing the above useful insecticidal compounds, a commercially feasible process for its purification is a prerequisite.

A conventionally well-known purification process for an aldehyde comprises converting the aldehyde into its aldehyde bisulfite adduct, separating it from non-aldehyde compounds, and decomposing it to recover the aldehyde [F. H. Allen and G. W. Lewbner, Org. Synth., Coll. Vol. 4, 866 (1963); G. B. Bochman, ibid., 2, 323 (1943)]. In the case of dealing with a strongly hydrophobic aldehyde such as 3-phenoxybenzaldehyde which is the objective compound of this invention, the reaction conditions as described below are considered to be necessary.

In converting a water-insoluble aldehyde into its aldehyde bisulfite adduct, the reaction system generally consists of substantially two phases, because an alkali metal or ammonium bisulfite is water-soluble but is not soluble in organic solvents. Accordingly, when it is expected to obtain the reaction product with a reasonable reaction rate and in a high yield, a measure frequently taken is to add to the reaction system an easily water-miscible solvent such as an alcohol to enable the reactants to readily contact each other. When such an organic solvent is used, the intended reaction product is isolated, after removal of the solvent by distillation, by dissolving the reaction mixture in water in the case of a water-soluble aldehyde bisulfite adduct and washing the aqueous layer with a water-insoluble solvent to remove oily non-aldehyde compounds; or, in the case of a crystalline aldehyde bisulfite adduct, by cooling the aqueous layer to precipitate the aldehyde bisulfite adduct which is then recovered by filtration. Moreover, since this reaction is reversible, a large amount of an alkali metal or ammonium bisulfite must be added to shift the equilibrium, aldehyde+alkali metal or ammonium bisulfite⇌aldehyde bisulfite adduct, to the right-hand side. In many cases, the amount, in moles, of an alkali metal or ammonium bisulfite used is 2 to 3 times the stoichiometric quantity or even more.

On applying the above-mentioned conventional purification process with a bisulfite to the case of 3-phenoxybenzaldehyde, the present inventors have found the following difficulties accompanied the process.

A crude aldehyde (containing about 80% of 3-phenoxybenzaldehyde and 20% of non-aldehyde compounds) was dissolved in toluene or chlorobenzene and contacted with an aqueous solution of sodium bisulfite (3 mole-equivalents to the aldehyde) for a long period of time with sufficient stirring under application of heat to obtain none of the aldehyde bisulfite adduct but the unreacted starting materials (Reference Example 2). When a water-soluble alcohol was used as an auxiliary solvent, as shown in Reference Example 3, conversion to the aldehyde bisulfite adduct was improved to some extent but not sufficiently and a large amount of unreacted 3-phenoxybenzaldehyde was recovered in very impure state from the filtrate. In this case, moreover, filterability of the crystals of sodium bisulfite adduct was too poor for the satisfactory isolation of the product by filtration on a commercial scale. And a decreased yield is effected from increased free aldehyde due to the significant solubility of the adduct in alcohol unfavorably shifting the equilibrium. The disadvantages listed above bring about much difficulty in commercialization of the conventional purification process in the present case.

The present inventors conducted studies to overcome the aforesaid difficulties and found unexpectedly that by use of an organic quaternary ammonium salt, an inorganic acid salt of organic tertiary amines, or a macrocyclic polyether as a catalyst, 3-phenoxybenzaldehyde bisulfite adduct of high purity in easily filterable form could be obtained in a high yield under mild conditions without using an auxiliary solvent such as an alcohol.

Based on this finding, the present invention has been accomplished.

Although the researches using organic quaternary ammonium salts and macrocyclic polyethers as phase transfer catalysts have become very active in recent years, no report on the addition reaction of an aldehyde and bisulfite as in the present invention, has been published.

In practicing the present invention, the reaction system comprises two phases, an aqueous one and an organic one. The amount of water to be used is not particularly limited. It is sufficient to use the minimal amount of water required for dissolving an alkali metal or ammonium bisulfite or metabisulfite, or to use suitable amount of water for keeping the crystals, which precipitate during the course of reaction, in a slurry form of suitable fluidity.

Since crude 3-phenoxybenzaldehyde is liquid, solvents are not necessarily used. However, it is not objectionable to use a solvent to facilitate the removal of impurities in filtering the bisulfite adduct. The solvents used as reaction medium are those which are difficultly soluble in water and have, as functional groups, neither a ketone nor an aldehyde group. Examples of suitable solvents are aromatic hydrocarbons such as benzene, toluene, xylene and ethylbenzene; halogenated aromatic hydrocarbons such as fluorobenzene, chlorobenzene, bromobenzene and dichlorobenzene; aliphatic or cycloaliphatic hydrocarbons such as pentane, hexane, heptane and cyclohexane; halogenated aliphatic hydrocarbons such as dichloromethane, chloroform, carbon tetrachloride, 1,1-dichloroethane, 1,2-difluoroethane, 1,1,1-trichloroethane, perchloroethylene, pentachloroethane, bromoform, 1,2-dibromoethane and 1,1,2,2-tetrabromoethane; and fatty acid esters such as ethyl acetate and the like. Mixtures of these solvents may also be used.

Because of the slightest solubility in water or in the above solvents, almost all the 3-phenoxybenzaldehyde bisulfite adduct formed by the reaction crystallizes out of the reaction system and shifts the reaction equilibrium to favor the formation of adduct. Accordingly, the amount of an alkali metal or ammonium bisulfite used as starting material can be greatly reduced as compared with the case of a conventional process. An approximately quantitative yield of the adduct may be obtained by using 1.0 to 1.5 moles of an alkali metal or ammonium bisulfite (or a half of this amount in the case of a metabisulfite) for 1 mole of 3-phenoxybenzaldehyde.

Alkali metal or ammonium bisulfite or metabisulfite in the present process includes sodium bisulfite, potassium bisulfite, sodium metabisulfite, potassium metabisulfite and ammonium bisulfite.

Non-limitative examples of compounds to be used as catalysts in the present process are listed below:

Organic quaternary ammonium salts represented by the general formula $R_1R_2R_3R_4NX$ (where $R_1$ represents an alkyl group having 1 to 20 carbon atoms which may be branched, phenyl group, benzyl group or 3-phenoxybenzyl group; $R_2$, $R_3$ and $R_4$, which may be the same or different, each represents an alkyl group having 1 to 12 carbon atoms which may be branched; and X represents a halogen atom or hydroxyl group).

That is, chlorides, bromides, iodides or hydroxides of benzyltriethylammonium, benzyltrimethylammonium, benzyltripropylammonium, phenyltriethylammonium, tetrabutylammonium, tetrapropylammonium, tetraethylammonium, tetramethylammonium, triethylpropylammonium, 3-phenoxybenzyltriethylammonium, cetyltrimethylammonium and the like.

Inorganic acid salts of organic tertiary amines.

That is, hydrochlorides, hydrobromides, sulfates, nitrates, sulfites, bisulfates or bisulfites of triethylamine, trimethylamine, triethanolamine, N-methylpyrrolidine, triethylenediamine and the like.

Macrocyclic polyethers [A. C. Knipe, J. Chem. Education, 53, 618 (1976)].

That is, 2,3,11,12-dibenzo-1,4,7,10,13,16-hexaoxacyclooctadeca-2,11-diene(dibenzo-18-crown-6), 2,3,11,12-dicyclohexyl-1,4,7,10,13,16-hexaoxacyclooctadecane(-dicyclohexyl-18-crown-6), 4,7,13,18-tetraoxa-1,10-diazabicyclo[8,5,5]eicosane, 4,7,13,16,21-pentaoxa-1,10-diazabicyclo[8,8,5]tricosane, 4,7,13,16,21,24-hexaoxa-1,10-diazabicyclo[8,8,8]hexacosane, and 5,6-benzo-4,7,13,16,21,24-hexaoxa-1,10-diazabicyclo[8,8,8]-hexacosane.

The amount of these catalysts to be added may be selected from the range of 1 to 300 millimole-equivalents to the reactant aldehyde, but in view of the reaction efficiency it is preferably selected from the range of 10 to 100 millimole-equivalents.

The reaction can be carried out at a temperature from about 0° to 80° C., but usually under a mild temperature condition of 10° to 60° C.

The 3-phenoxybenzaldehyde bisulfite adduct formed by the reaction crystallizes in an easily filterable form and can be collected by suitable means such as vacuum filtration, pressure filtration, centrifugal filtration and the like. If necessary, small amounts of non-aldehyde organic substances adhered to the crystals can be removed by washing with an organic solvent.

The 3-phenoxybenzaldehyde alkali metal or ammonium bisulfite adduct formed according to this invention is decomposed to yield purified 3-phenoxybenzaldehyde by treating in known ways such as treating with inorganic acids such as, for example, hydrochloric, sulfuric, nitric, sulfurous, and phosphoric acids, organic acids such as, for example, acetic acid and formic acid, or bases such as, for example, alkali metal hydroxides, e.g. sodium hydroxide, potassium hydroxide, and ammonium hydroxide, and carbonates, e.g. sodium carbonate, potassium carbonate, sodium bicarbonate, and potassium bicarbonate [F. H. Allen and G. W. Lewbner, Org. Synth., Coll. Vol. 4, 866 (1963); G. B. Bochman, ibid. 2, 323 (1943)].

As described in the foregoing, compared with the conventional process which involves troublesome operations of removing the alcohol by distillation and recovering it, the present process makes it possible to reduce the amount of alkali metal or ammonium used and to select freely the reaction medium. Further, according to this invention, owing to a favorable volume utilization factor of the equipment, highly purified 3-phenoxybenzaldehyde can be produced more simply and economically on a commercial scale.

The invention is illustrated below in further detail with reference to Reference Examples and Examples, but the invention is not limited to these examples.

REFERENCE EXAMPLE 1

[S. J. Angyal, Organic Reactions, Vol. 8, 197 (1954)]

(1) To 82 g of 3-phenoxybenzyl bromide-hexamethylenetetramine addition product (0.19 mole), were added 70 ml of glacial acetic acid and 70 ml of water and the mixture was refluxed for 8 hours with heating.

After being cooled to room temperature, the reaction mixture was extracted twice with 60 ml of dichloromethane and the organic layer was washed with 50 ml of water, freed from the dichloromethane by distillation to obtain 38 g of a crude product containing 77.0% of 3-phenoxybenzaldehyde. (as determined by GC-IS method using dibutyl terephthalate as internal standard).

(2) A known process for preparing 3-phenoxybenzaldehyde [G. Lock and F. H. Kempter, Monatsh., 67, 24 (1935)].

The reaction proceeds according to the following scheme:

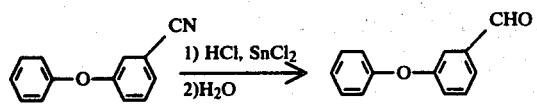

Hydrogen chloride was introduced until saturation into a solution of 37.9 g of anhydrous stannous chloride (0.2 mole) in 200 ml of anhydrous ether. To the resulting solution, was added 19.5 g of 3-phenoxybenzonitrile (0.1 mole) and the mixture was stirred for 10 hours at room temperature. After addition of 200 ml of water and thorough stirring, the insoluble matter was removed by filtration. The filtrate was separated and the ether layer was further washed three times with 50 ml of water. After removal of the ether by distillation, the residue was distilled to obtain 8.5 g of crude 3-phenoxybenzaldehyde boiling at 100° to 115° C./0.45 mmHg which contained 71.4% of 3-phenoxybenzaldehyde.

REFERENCE EXAMPLE 2

To 280 g of a 20% aqueous solution of sodium bisulfite (0.538 mole of sodium bisulfite), was added dropwise a solution containing 45.0 g of crude 3-phenoxybenzaldehyde (79.7% purity (0.181 mole of 3-phenoxybenzaldehyde) and containing no other aldehyde compounds) in 90 g of chlorobenzene, taking 2 hours with stirring at room temperature. Because no crystals deposited from the reaction system, the reaction temperature was elevated to 60° C. and stirring was continued at his temperature for a further 5 hours. No crystal deposit was observed. The reaction was discontinued and the reaction solution was separated. The organic layer was freed from the chlorobenzene to recover 44.3 g of crude 3-phenoxybenzaldehyde of 77.8% purity.

REFERENCE EXAMPLE 3

To a solution prepared by mixing 160 g of a 15% aqueous solution of sodium bisulfite (0.231 mole of sodium bisulfite) and 160 ml of methanol, was added 14.0 g of an organic mixture containing 54.0% of 3-phenoxybenzaldehyde (0.038 mole of 3-phenoxybenzaldehyde) and no other aldehyde compounds. The resulting mixture was stirred at 70° C. for 4 hours. The reaction mixture was freed from the methanol by distillation and cooled to room temperature. The precipitated white crystals were collected by filtration and washed three times with 30 ml of ethanol to obtain 10.9 g (94.8% yield) of white crystals. After removal of the ethanol, the filtrate was extracted with 50 ml of ethyl acetate and the separated aqueous layer was removed. On removing the ethyl acetate by distillation, there was obtained 7.1 of a concentrated residue containing 12.0% of 3-phenoxybenzaldehyde.

To a mixture comprising 40 g of a 5% aqueous sodium hydroxide solution and 15 ml of toluene, was added 10.0 g of the 3-phenoxybenzaldehyde-sodium bisulfite adduct obtained above. The resulting mixture was stirred for 2 hours at room temperature under a nitrogen stream. After settling, the aqueous layer was removed. The toluene layer was washed with 5 ml of 1% hydrochloric acid and then with an aqueous sodium chloride solution. After removal of the toluene by distillation, there was obtained 6.0 g (90.9% yield) of a colorless, clear liquid containing 96.7% of 3-phenoxybenzaldehyde.

EXAMPLE 1

To a solution prepared by dissolving 2.3 g of benzyltriethylammonium chloride (0.010 mole) in 123.3 g of a 20% aqueous solution of sodium bisulfite (0.237 mole of sodium bisulfite), while being stirred at room temperature, was added dropwise taking 2 hours a solution prepared by dissolving 45.0 g of crude 3-phenoxybenzaldehyde (79.7% purity (0.181 mole of 3-phenoxybenzaldehyde) and containing no other aldehyde compounds) in 90 g of chlorobenzene. Immediately after the starting of the dropwise addition, white crystals began to precipitate out of the reaction system. After completion of the dropwise addition, stirring was continued for a further two hours. The crystals were then collected by filtration, washed three times with 45 g of chlorobenzene, and dried to obtain 53.0 g (98.3% yield) of 3-phenoxybenzaldehydesodium bisulfite adduct.

To a mixture comprising 158.8 g of a 5% aqueous sodium hydroxide solution and 60 ml of toluene, was added 40.0 g of the 3-phenoxybenzaldehyde sodium bisulfite adduct (0.132 mole) obtained above. The resulting mixture was stirred for 2 hours at room temperature under a nitrogen stream. After settling and removal of the aqueous layer, the toluene layer was washed with 20 ml of 1% hydrochloric acid and then with an aqueous sodium chloride solution. On removal of the toluene, there was obtained 25.4 g (96.9% yield) of a colorless, clear liquid containing 98.5% of 3-phenoxybenzaldehyde.

EXAMPLE 2

To a solution prepared by dissolving 1.3 g of triethylamine hydrochloride (0.009 mole) in 69.2 g of a 35.8% aqueous solution of sodium bisulfite (0.238 mole of sodium bisulfite) while being stirred at room temperature, was added dropwise taking 2 hours a solution prepared by dissolving 50 g of crude 3-phenoxybenzaldehyde (72.5% purity (0.183 mole of 3-phenoxybenzaldehyde) and containing no other aldehyde compounds) in 80 g of toluene. Immediately after the starting of the dropwise addition, white crystals began to precipitate out of the reaction system. After completion of the addition, stirring was continued for a further 2 hours. The crystals were collected by filtration, washed three times with 50 g of toluene, and dried to obtain 54.5 g (98.5% yield) of 3-phenoxybenzaldehyde sodium bisulfite adduct.

To 40.0 g of the above adduct (0.132 mole), was added 90 g of water. To the resulting mixture, while being refluxed by heating, was added dropwise taking one hour 15 g of 50% sulfuric acid. The sulfur dioxide evolved during the reaction was removed by absorption with a 10% aqueous sodium hydroxide solution. After completion of the dropwise addition, refluxing was continued for 30 minutes. The reaction mixture was cooled to room temperature and extracted with 50 ml of toluene. The toluene layer was washed twice with 15 ml of water and concentrated to obtain 25.2 g (96.0% yield) of a colorless, clear liquid containing 98.1% of 3-phenoxybenzaldehyde.

In the following table are shown other Examples, wherein various organic solvents, catalysts, and bisulfites or metabisulfites were employed, other conditions having been similar to those in Example 1.

| Example No. | Solvent | Catalyst | Molar ratio of catalyst (*1) | Bisulfite or meta-bisulfite | Molar ratio of bisulfite or meta-bisulfite (*1) | Yield of adduct (%) | Purity (*2) |
|---|---|---|---|---|---|---|---|
| 3 | Xylene | Tetrabutylammonium bromide | 0.05 | NaHSO$_3$ | 1.2 | 96.8 | 99.1 |
| 4 | Benzene | Cetyltrimethyl-ammonium chloride | 0.05 | KHSO$_3$ | 1.3 | 99.1 | 98.2 |
| 5 | Heptane | Dibenzo-18-crown-6 | 0.04 | NaHSO$_3$ | 1.4 | 98.3 | 98.4 |
| 6 | Perchloro-ethylene | 4,7,13,18-Tetraoxa-1,10-diazabicyclo-[8,8,5]eicosane | 0.04 | Na$_2$S$_2$O$_5$ | 0.7 | 97.0 | 98.8 |
| 7 | None | Benzyltrimethyl-ammonium bromide | 0.03 | NaHSO$_3$ | 1.3 | 97.3 | 97.5 |
| 8 | Benzene | Tetraethylammonium bromide | 0.01 | NaHSO$_3$ | 1.4 | 97.3 | 98.2 |
| 9 | Toluene/heptane (1/1) | Benzyltriethyl-ammonium chloride | 0.05 | NaHSO$_3$ | 1.4 | 99.7 | 97.9 |
| 10 | Chloroform | Benzyltriethyl-ammonium hydroxide | 0.05 | Na$_2$S$_2$O$_5$ | 0.6 | 97.2 | 98.3 |
| 11 | Chloro-benzene | 3-Phenoxybenzyltri-ethylammonium bromide | 0.03 | Na$_2$S$_2$O$_5$ | 0.7 | 98.6 | 97.9 |
| 12 (*3) | Toluene | N-methylpyrrolidine sulfate | 0.08 | NH$_4$HSO$_3$ | 1.5 | 98.5 | 97.3 |
| 13 | Xylene | Triethylamine bisulfite | 0.03 | KHSO$_3$ | 1.4 | 99.0 | 98.0 |
| 14 | 1,2-Di-chloro-ethane | Dodecylbenzyl-diethylammonium chloride | 0.02 | Na$_2$S$_2$O$_5$ | 0.7 | 97.3 | 98.0 |
| 15 (*4) | Benzene/ethyl acetate (1/1) | Tetrapropylammonium bromide | 0.10 | Na$_2$S$_2$O$_5$ | 0.7 | 97.9 | 97.8 |
| 16 (*5) | Chloro-benzene/perchloro-ethylene (2/1) | Phenyltriethylammo-nium iodide | 0.06 | KHSO$_3$ | 1.3 | 98.5 | 97.9 |

Note:
(*1) Molar ratios of catalyst and bisulfite or metabisulfite are based on 3-phenoxybenzaldehyde.
(*2) Purity of the 3-phenoxybenzaldehyde obtained by decomposition of the adduct in an ordinary way.
(*3) Reaction temperature in Example 12 was 45° C.
(*4) Reaction temperature in Example 15 was 10° C.
(*5) Reaction temperature in Example 16 was 60° C.

What is claimed is:

1. A process of purifying 3-phenoxybenzaldehyde which comprises reacting crude 3-phenoxybenzaldehyde with an alkali metal or ammonium bisulfite or a metabisulfite in the presence of an organic quaternary ammonium salt, an inorganic acid salt of organic tertiary amines or a macrocyclic polyether as a catalyst, isolating the resulting 3-phenoxybenzaldehyde bisulfite adduct, and decomposing it by using an acid or a base or by heating, wherein the molar ratio of the catalyst to 3-phenoxybenzaldehyde is from 0.001 to 0.3, wherein the molar ratio of the alkali metal or ammonium bisulfite to 3-phenoxybenzaldehyde is from 1.0 to 1.5 and the molar ratio of the metabisulfite to 3-phenoxybenzaldehyde is from 0.5 to 0.75, wherein the reaction temperature is 0° to 80° C., and wherein the reaction medium is water or a mixture of water and a difficulty water-soluble solvent containing neither ketone group nor aldehyde group, wherein the organic quaternary ammonium salt has the formula $R_1R_2R_3R_4NX$ in which $R_1$ is a straight-chain or branched alkyl having 1 to 20 carbon atoms, phenyl, benzyl or 3-phenoxybenzyl, $R_2$, $R_3$ and $R_4$ are a straight-chain or branched alkyl having 1 to 12 carbon atoms which may be the same or different and X is halogen or hydroxyl; wherein the organic acid salt of the organic tertiary amine is a hydrochloride, hydrobromide, sulfate, nitrate, sulfite bisulfate, or bisulfite of triethylamine, trimethylamine, triethanolamine, N-methylpyrrolidine, or triethylenediamine; and wherein the macrocyclic polyether is 2,3,11,12-dibenzo-1,4,7,10,13,16-hexaoxacyclooctadeca-2,11-diene(dibenzo-18-crown-6), 2,3,11,12-dicyclohexyl-1,4,7,10,13, 16-hexaoxacyclooctadecane(dicyclohexyl-18-crown-6), 4,7,13,18-tetraoxa-1,10-diazabicyclo[8,5,5]eicosane, 4,7,13,16,21-pentaoxa-1,10-diazabicyclo[8,8,5]tricosane, 4,7,13,16,21,24-hexaoxa-1,10-diazabicyclo[8,8,8]hexacosane, or 5,6-benzo-4,7,13,16,21, 24-hexaoxa-1,10-diazabicyclo[8,8,8]-hexacosane.

2. A process according to claim 1, wherein the molar ratio of the catalyst to 3-phenoxybenzaldehyde is from 0.01 to 0.1.

3. A process according to claim 1, wherein the reaction temperature is 10° to 60° C.